United States Patent [19]

Habu et al.

[11] Patent Number: 4,933,508

[45] Date of Patent: Jun. 12, 1990

[54] METHOD FOR PRODUCING A CYCLOALKANOL

[75] Inventors: Haruo Habu, Kitakyushu; Kouji Watanabe, Mizumaki; Takeshi Matsuoka, Kitakyushu, all of Japan

[73] Assignee: Mitsubishi Kasei Corporation, Tokyo, Japan

[21] Appl. No.: 248,084

[22] Filed: Sep. 23, 1988

[30] Foreign Application Priority Data

Sep. 24, 1987 [JP] Japan .................................. 62-239474

[51] Int. Cl.$^5$ ........................ C07C 35/08; C07C 35/00
[52] U.S. Cl. .................................... 568/832; 568/700; 568/821; 568/822; 568/834; 568/835; 568/838

[58] Field of Search ............... 568/470, 475, 835, 700, 568/821, 822, 838, 834, 837

[56] References Cited

U.S. PATENT DOCUMENTS 3,497,544 2/1970 Russell ................................ 568/835
3,609,176 9/1971 Alay .................................... 568/835

Primary Examiner—Werren B. Lone
Attorney, Agent, or Firm—Oblon, Spivak, McClelland, Maier & Neustadt

[57] ABSTRACT

A method for producing a cycloalkanol, which comprises oxidizing a cycloalkane with a molecular oxygen-containing gas in a liquid phase in the presence of a catalyst, wherein an aromatic nitro compound is present in the oxidation reaction system.

15 Claims, No Drawings

METHOD FOR PRODUCING A CYCLOALKANOL

BACKGROUND OF THE INVENTION

1. Field of the Invention

The present invention relates to a method for producing a cycloalkanol advantageously on an industrial scale by oxidizing a cycloalkane with molecular oxygen in a liquid phase.

2. Discussion of the Background

For the production of cycloalkanols, it is known to oxidize cycloalkanes with a molecular oxygen-containing gas in the liquid phase in the presence of a catalyst such as a heavy metal compound or a boron compound. Such a method is widely used on an industrial scale, since the selectivity for the corresponding cycloalkanols or cycloalkanones is high.

However, if it is attempted to increase the conversion of cycloalkanes by such a method, economically or operationally undesirable phenomena, such as a substantial decrease of the selectivity or an increase of the formation of tar, appear. Therefore, it is common to set the conversion of cycloalkanes at a level of from 3 to 10%, and it has been proposed to use various co-catalysts or additives in order to improve the selectivity for the total of cycloalkanols and cycloalkanones. However, no adequate effects have been thereby obtained.

SUMMARY OF THE INVENTION

Under these circumstances, the present inventors have conducted research with an aim to further improve the selectivity for the desired compound in a method for oxidizing a cycloalkane in a liquid phase in the presence of a conventional catalyst As a result, it has been found that the selectivity for a cycloalkanol can be improved by as much as a few percents by the presence of an aromatic nitro compound in the reaction system. The present invention has been accomplished on the basis of this discovery.

DETAILED DESCRIPTION OF THE PREFERRED EMBODIMENTS

The present invention provides a method for producing a cycloalkanol, which comprises oxidizing a cycloalkane with a molecular oxygen-containing gas in a liquid phase in the presence of a catalyst, wherein an aromatic nitro compound is present in the oxidation reaction system.

Now, the present invention will be described in detail.

The cycloalkane which may be used as the starting material in the present invention, is usually a 3- to 12-membered cycloalkane, which may have a branched chain.

Specifically, it includes cyclopropane, cyclobutane, cyclopentane, cyclohexane, cyclooctane, cyclododecane, methylcyclopentane, methylcyclohexane, dimethylcyclohexane, decahydronaphthalene, tetralin, cyclohexylbenzene and dicyclohexylhexane. Particularly preferred is cyclohexane.

The catalyst for the oxidation reaction may be a conventional catalyst such as a boron compound or a cobalt compound. Specific examples of the boron compound may usually be a boric acid such as orthoboric acid, metaboric acid, tetraboric acid or boric anhydride, and a boric acid ester such as trimethyl borate or tributyl borate. Among them, a boric acid is preferred. Such a boron compound is used usually in an amount of at least $\frac{1}{3}$ mol as boron per mol of the cycloalkanol formed by the oxidation. When the reaction is conducted in a batch system, the boron compound may be used in large excess, because it may be present in a solid form without presenting any trouble. However, when the reaction is conducted in a continuous system, it is advisable to minimize the solid state boron compound in order to avoid clogging of the apparatus or other inconveniences, and it is usually advisable to select the amount within a range of from 0.5 to 5 mol as boron per mol of the cycloalkanol.

Specific examples of the cobalt compound include cobalt acetate, cobalt chloride, cobalt sulfate, cobalt naphthenate, cobalt octanoate, cobalt laurate, cobalt palmitate, cobalt stearate, cobalt acetylacetonate and a mixture thereof. Such a cobalt compound may be used usually in an amount of from 0.001 to 100 ppm, preferably from 0.5 to 5 ppm as a cobalt ion concentration in the reaction mixture.

In the present invention, it is essential that an aromatic nitro compound is present in the oxidation reaction system of a cycloalkane. Namely, by the presence of the aromatic nitro compound, it is possible to improve the selectivity of the desired reaction product.

The aromatic nitro compound to be used in the present invention may usually be a mononitro compound, a dinitro compound or a trinitro compound of a carbon monocyclic or carbon condensed polycyclic compound containing a carbon 6-membered aromatic ring, such as a benzene ring, a naphthalene ring, a naphthoquinone ring, an anthracene ring or an anthraquinone ring. Among such aromatic nitro compounds, a dinitro compound and a trinitro compound are preferred from the viewpoint of the effectiveness. However, these compounds are usually unstable and difficult to handle. Practically, a mono- or di-nitro compound is preferred. On the other hand, as the aromatic ring, a benzene ring, a naphthalene ring or an anthraquinone ring is usually preferred. Further, in the present invention, it is also possible to employ an aromatic nitro compound substituted by a suitable substituent which does not adversely affect the reaction. As such a substituent, for example, a lower alkyl group, a hydroxyl group, a lower alkoxy group, an amino group, a halogen atom or a carboxyl group may be mentioned.

Specific examples of the aromatic nitro compound include mononitro compounds such as nitrobenzene, nitrotoluene, chloronitrobenzene, dichloronitrobenzene, nitrobenzoic acid, nitrophthalic acid, nitronaphthalene and nitroanthraquinone; dinitro compounds such as dinitrobenzene, dinitrotoluene, dinitrophenol, dinitrochlorobenzene, dinitrobenzoic acid, dinitronaphthalene, dinitroanthracene and dinitroanthraquinone; trinitro compounds such as trinitrobenzene; and mixtures thereof. There is no particular restriction as to the positions of nitro groups substituted on the aromatic ring, and such positions may be o-, m- or p-positions.

The aromatic nitro compound is present in the reaction system usually in an amount of from 5 to 50,000 ppm, preferably from 10 to 10,000 ppm relative to the starting material cycloalkane. If the amount is too small, no adequate effect of the present invention can be obtained. On the other hand, if the amount is excessive, no additional effect can be obtained, and such is not economical.

The molecular oxygen-containing gas to be used for the oxidation may usually be oxygen, air or a gas obtained by diluting oxygen or air with an inert gas. Usually, air may be employed. The oxygen concentration should preferably be relatively low. It is usually preferred to employ a gas having an oxygen concentration of from 5 to 25% by volume.

The oxidation reaction is conducted usually at a temperature of from 100° to 250° C., preferably from 140° to 180° C. If the temperature is too low, the oxidation reaction does not proceed. On the other hand, if the temperature is too high, the formation of by-products increases, such being undesirable.

The reaction pressure may be atmospheric pressure or an elevated pressure. It may suitably be selected taking into consideration the vapor pressure and the oxygen partial pressure at the reaction temperature of the starting material cycloalkane. It is usually not higher than 100 kg/cm$^2$G, preferably from 5 to 25 kg/cm$^2$G. The pressure is preferably raised by an inert gas such as nitrogen.

The method of the present invention can be conducted in a batch system, a semi-batch system or a continuous system in accordance with a well known operational method. For example, in a case where the method is conducted in a continuous system using a boron compound, while the catalyst and a cycloalkane containing the aromatic nitro compound of the present invention are supplied to an agitation tank having a gas supply tube, a gas discharge tube and an overflow tube, oxygen or an oxygen-containing gas is introduced from the gas supply tube so as to attain a predetermined cycloalkane conversion, and the reaction is conducted by withdrawing water formed by the reaction and an unreacted cycloalkane from the gas discharge tube together with an exhaust gas and withdrawing the reaction solution from the overflow tube while controlling the temperature and the pressure in the tank.

In the present invention, when a boron compound is used as the catalyst, the reaction mixture obtained by the oxidation is usually composed mainly of a hydroperoxide and a boric acid ester of the cycloalkanol. As other oxidation reaction products, various kinds of oxidation reaction products are contained which include, for example, cycloalkanones, oxycarboxylic acids, dicarboxylic acids, diols, oxycarboxylic esters, dicarboxylic acid esters and lower alcohols.

However, the hydroperoxide and the boric acid ester of the cycloalkanol can readily be converted to the corresponding cycloalkanol by a treatment in accordance with a conventional method. For example, by the heat treatment at a temperature of from 100° to 250° C., followed by the hydrolysis at a temperature of from room temperature to 100° C., the desired product can easily be recovered.

Now, the present invention will be described in further detail with reference to Examples. However, it should be understood that the present invention is by no means restricted to such specific Examples.

EXAMPLE 1

Into an autoclave equipped with a gas supply tube, a gas discharge tube, a starting material liquid supply tube, a liquid discharge tube, a stirrer and an overflow tube located at a liquid volume level of 1.0 liter and having an internal capacity of 1.5 liter, 650 g of cyclohexane and 13.0 g of metaboric acid were charged, and the temperature and the pressure were raised to 165° C. and 10 kg/cm$^2$G, respectively.

Then, a gas mixture comprising 5.0% by volume of oxygen and 95.0% by volume of nitrogen was blown thereinto. After confirming that the oxygen concentration in the gas phase became to be not higher than 1%, the mixed gas was switched to air, and air was continuously blown thereinto at a rate of 0.65 liter/min. from the starting material liquid supply tube. Cyclohexane containing 2.0% by weight of metaboric acid and the aromatic nitro compound in the amount as identified in Table 1, was continuously supplied at a rate of 16.7 g/min. The oxidation reaction was conducted at 165° C. under pressure of 10 kg/cm$^2$G while withdrawing an exhaust gas containing water, cyclohexane, etc. from the gas discharge tube and withdrawing the liquid phase from the overflow tube. Then, the withdrawn reaction mixture was subjected to heat treatment at 165° C. for 30 minutes. Then, water was added thereto in the same amount as the reaction solution, followed by hydrolysis at 60° C. for 30 minutes.

Upon expiration of 5 hours since the reaction system entered in a stationary state, the gas phase and the liquid phase were analyzed by gas chromatography and liquid chromatography, respectively, whereby the conversion of cyclohexane was 3.6%, the selectivity for cyclohexanol was 85.2%, and the selectivity for cyclohexanone was 6.6%. The selectivity for the total of cyclohexanol and cyclohexanone was 91.8%.

EXAMPLES 2 to 10

The oxidation reaction was conducted in the same manner as in Example 1 except that the compound identified in Table 1 was used instead of m-dinitrobenzene as the aromatic nitro compound.

Cyclohexanone in the reaction products is an effective component as well as cyclohexanol which is the desired product of the present invention. Therefore, in Table 1, the selectivity for the total of cyclohexanone and cyclohexanol was presented. The amount of cyclohexanone was roughly from 1/12 to 1/13 of the amount of cyclohexanol.

COMPARATIVE EXAMPLE 1

The oxidation reaction was conducted in the same manner as in Example 1 except that no aromatic nitro compound was present. The results are shown in Table 1.

TABLE 1

|  | Aromatic nitro compound | | Conversion of cyclohexane (%) | Selectivity[2] (%) |
| --- | --- | --- | --- | --- |
|  | Type | Amount[1] (ppm) | | |
| Example 1 | m-Dinitrobenzene | 200 | 3.6 | 91.8 |
| Example 2 | m-Dinitrobenzene | 20 | 3.5 | 90.9 |
| Example 3 | p-Dinitrobenzene | 100 | 3.5 | 91.6 |
| Example 4 | 2,4-Dinitrotoluene | 100 | 3.5 | 91.0 |
| Example 5 | 2,4-Dinitrophenol | 100 | 3.6 | 91.0 |
| Example 6 | 1,5-Dinitroanthraquinone | 100 | 3.5 | 91.2 |
| Example 7 | Nitrobenzene | 100 | 3.5 | 90.4 |
| Example 8 | p-Chloronitrobenzene | 50 | 3.5 | 90.8 |
| Example 9 | 2,5-Di- | 50 | 3.4 | 90.8 |

TABLE 1-continued

|  | Aromatic nitro compound | | Conversion of cyclohexane (%) | Selectivity[2] (%) |
| --- | --- | --- | --- | --- |
|  | Type | Amount[1] (ppm) | | |
| Example 10 | chloronitrobenzene 1-Nitronaphthalene | 100 | 3.5 | 90.4 |
| Comparative Example 1 | No addition | — | 3.5 | 89.6 |

Notes:
[1]The proportion of the aromatic nitro compound relative to cyclohexane.
[2]The selectivity for the total of cyclohexanol and cyclohexanone.

According to the method of the present invention, an aromatic nitro compound is present in the reaction system for oxidizing a cycloalkane with a molecular oxygen containing gas in a liquid phase in the presence of a catalyst such as a boron compound, whereby it is possible to improve the selectivity (the selectivity for cyclohexanol and cyclohexanone) by from 1 to 2% as compared with the case where no aromatic nitro compound was added, at the same level of the cycloalkane conversion. The industrial value of the method of the present invention is substantial since a cycloalkanol and a cycloalkanone such as cyclohexanol and cyclohexanone are produced in an extremely large industrial scale.

We claim:

1. In a method for producing a cycloalkanol comprising oxidizing a cycloalkane with a molecular oxygen-containing gas in the liquid phase in the presence of a boron compound or cobalt compound catalyst, the improvement wherein an aromatic nitro compound is present in the oxidation reaction system, wherein said aromatic nitro compound is a mononitro compound, a dinitro compound or a trinitro compound of a carbon monocyclic or carbon condensed polycyclic compound containing a carbon six-membered aromatic ring which is unsubstituted or substituted by a lower alkyl group, a hydroxyl group, a lower alkoxy group, an amino group, a halogen atom or a carboxyl group.

2. The method according to claim 1, wherein the aromatic nitro compound is present in the reaction system in an amount of from 5 to 50,000 ppm relative to the starting material cycloalkane.

3. The method according to claim 1, wherein the aromatic nitro compound is a carbon monocyclic or carbon condensed polycyclic aromatic nitro compound.

4. The method according to claim 1, wherein the aromatic nitro compound is a mononitro compound of benzene, naphthalene or anthraquinone.

5. The method according to claim 1, wherein the aromatic nitro compound is a dinitro compound of benzene, naphthalene or anthraquinone.

6. The method according to claim 1, wherein the aromatic nitro compound is a nitrobenzene which is unsubstituted or substituted by a lower alkyl group, a hydroxyl group, a lower alkoxy group, an amino group, a halogen atom or a carboxyl group.

7. The method according to claim 1, wherein the aromatic nitro compound is unsubstituted mononitrobenzene.

8. The method according to claim 1, wherein the catalyst is a boron compound.

9. The method according to claim 1, wherein the catalyst is a boric acid.

10. The method according to claim 8, wherein the catalyst of a boron compound is used in an amount of from 0.5 to 5 mols as boron per mol of the resulting cycloalkanol.

11. The method according to claim 1, wherein the cycloalkane is cyclohexane.

12. The method according to claim 1, wherein the reaction temperature is from 100° to 250° C.

13. The method according to claim 1, wherein the reaction pressure is from 5 to 25 kg/cm$^2$G.

14. The method according to claim 1, wherein the molecular oxygen-containing gas has an oxygen concentration of from 5 to 25% by volume.

15. The method according to claim 1, wherein the molecular oxygen-containing gas is air.

* * * * *